United States Patent [19]

Forbes

[11] Patent Number: 4,856,535

[45] Date of Patent: Aug. 15, 1989

[54] PROTECTIVE FACE SHIELD

[76] Inventor: Christopher B. Forbes, 3737 Saint Johns Bluff Rd. #203, Jacksonville, Fla. 33216

[21] Appl. No.: 125,206

[22] Filed: Nov. 25, 1987

[51] Int. Cl.⁴ .............................................. A61F 13/00
[52] U.S. Cl. .......................................... 128/857; 2/9
[58] Field of Search ................. 2/9, 11, 173, 174, 206, 2/209.5, 274; 128/132 R, 206.14, 206.18, 206.19, 206.25, 88.5, 206.27, 201.23

[56] References Cited

U.S. PATENT DOCUMENTS

| | | | |
|---|---|---|---|
| 3,015,105 | 1/1962 | Rogowski | 2/9 |
| 3,041,624 | 7/1962 | Cutrona, Jr. | 2/11 |
| 3,060,445 | 10/1962 | Brockman | 2/9 |
| 3,137,006 | 6/1964 | Berlind | 2/9 |
| 3,310,812 | 3/1967 | Gaisser | 2/9 |
| 4,240,420 | 12/1980 | Riaboy | 128/206.14 |
| 4,467,799 | 8/1984 | Steinberg | 128/206.14 |

FOREIGN PATENT DOCUMENTS 119914 4/1901 Fed. Rep. of Germany ... 128/132 R

Primary Examiner—Robert A. Hafer
Assistant Examiner—Charles H. Sam
Attorney, Agent, or Firm—Breneman & Georges

[57] ABSTRACT

A post operative protective face shield comprises essentially a transparent body of a flexible material. Along the upper and side edges of the body of the face shield is provided an adhesive strip whereby the shield can be adhesively attached to the perimeter of the face of a patient. The shield is attached to the forehead adjacent the hairline and extending downwardly following the contour along the sides of the face. The shield is primarily adapted for providing a waterproof shield to allow a patient having recently had facial cosmetic or reconstructive surgery to shower and shampoo their hair while keeping the bandages and incisions in a clean dry condition.

17 Claims, 2 Drawing Sheets

PROTECTIVE FACE SHIELD

BACKGROUND OF THE INVENTION

1. Field of the Invention

The present invention relates to a light weight disposable protective shield to cover and protect the face and eyes of the wearer during showers to maintain a dry environment after eye or face surgery. More particularly the invention is directed to a transparent face conforming protective shield for wearing in the shower after facial surgery to allow the patient to bathe without exposing the bandages, sutures or incisions to water and protecting any incisions or splints on the face thereby allowing proper healing.

2. Description of the Prior Art

Reconstructive and cosmetic surgery has been used in recent years with increasing regularity and success. The success of this type of surgery is dependent on many factors of which perhaps the most important is the proper sterile environment for healing of the facial tissue along with the mental attitude of the patient. The mental attitude or outlook of the patient is improved when the patient can return to normal activities as quickly as possible after surgery such as bathing and taking showers.

The generally employed method of maintaining a proper healing environment after cosmetic or reconstructive surgery is to apply sterile bandages which must be regularly changed. The patient often times finds these bandages uncomfortable and burdensome. The bandages particularly create difficulties during haircuts, showering and shampooing since it is essential that the bandage remain in a dry sterile condition.

In the past it has been necessary to direct the spray of water during showering and shampooing in such a manner to avoid the wetting of the patient's face and bandages. This is of course a difficult task and it is not always possible to keep the facial area completely dry due to the overspray of the shower nozzle. There is thus a need for a device which will effectively and comfortable seal against the patient's forehead and face to ensure a dry environment during showering or during haircuts.

Numerous prior art devices have been used to protect the face from aerosol sprays and contaminants during various procedures. These devices generally however do not provide complete protection or an adequate seal around the face to ensure a dry sterile environment. Examples of masks which are retained in place by mechanical devices such as hair nets, ties and ear pieces include Diss, U.S. Pat. Nos. 2,355,283, Brockman 3,060,455, Tate 2,249,734 and Rogowski 3,015,105. These devices cover the face and hair primarily to protect them from garments or the face from hairsprays.

The arrangement disclosed in the prior art devices does not effectively protect the patient's face during showering or shampooing since none of the devices provide a water tight seal around the perimeter of the face. In addition the manner in which these devices are retained in place do not permit adequate cleaning of the hair or scalp without removing the device thereby subjecting the patient to risk by exposing or uncovering their face and the bandages.

Some of the prior art devices have attempted to form a seal around the face or a portion of the face by means of a flexible sealing element for the purpose of providing a dust free environment. An example of such a device is disclosed in Holloway U.S. Pat. No. 3,545,436. This type of face mask device is cumbersome and as with the other prior art devices must be attached by straps, ties or hooks thereby limiting its use in shampooing or showering. Additionally, the sealing element is intended to prevent the infiltration of particulates and is not designed to keep the facial area dry.

Examples of other filtering masks which cover the nose and mouth area of a user are disclosed in Steinberg U.S. Pat. Nos. 4,467,799 and Brevik 3,695,265. These devices are retained on the face by applying selected areas with a small amount of adhesive generally on the bridge of the nose and cheeks. These devices do not provide complete coverage of the face and are not capable of providing an adequate water tight seal to keep the area under the mask dry and sterile during showering.

A further example of prior art mask devices is Sweasingen U.S. Pat. No. 2,809,633. This device pertains to an aviation oxygen mask to supply oxygen to the pilot during high altitude flying. The mask includes a conical shaped member to cover the nose and mouth areas of the face and is held in place by a pressure sensitive adhesive strip surrounding the edge of the mask. This type of mask is not intended and is not suitable for use in the shower since the mask is not able to protect the entire face of a patient.

Further examples of the prior art include Geany U.S. Pat. No. 4,004,584 relating to a porous nasal filter device adhesively attached to the area around the nostrils. This porous type of filter device is not capable of protecting any portion of the face and keeping the area dry during showering.

There is thus a need for a device which is capable of being comfortably worn by a patient which will form an effective water tight seal to cover and protect the desired areas of the face and eyes after cosmetic or reconstructive surgery. There is further a need for a waterproof face shield which is inexpensive, light weight and easy to apply and remove without hindering the ability of the patient to shower and shampoo effectively and comfortably.

The present invention is accordingly directed to a clear light weight waterproof face shield which can be easily applied comfortably worn and safely removed by a patient after cosmetic or reconstructive surgery. The novel face shield can be quickly placed over the face to provide effective protection from the spray during showering or shampooing thereby maintaining the bandages and the skin in a clean and dry condition. The demands of post-operative care have required a device capable of providing a dry environment which is inexpensive, lightweight and disposable.

SUMMARY OF THE INVENTION

The disadvantages and limitations of the prior art devices for protecting the face are obviated while providing for the effective protection of the face and eyes during showering and shampooing. The device according to the invention is of a transparent flexible material which can be readily formed to the contour of the patient's face and is able to form an effective water tight seal against the skin.

The present invention provides a combination of elements which enable a patient to quickly attach the shield to the patient's face in a manner providing a continuous seal which can be worn in the shower and will maintain the patient's face in a clean dry condition.

The novel device includes a sheet of thin transparent and flexible light weight plastic material cut into a predetermined shape to enable the device to conform to the patient's face.

The shield according to the preferred embodiment of the invention includes a pressure sensitive adhesive strip around the edge which is used to secure the shield in place. The edge of the shield having the adhesive is, in the preferred form, pressed against the patient's forehead adjacent the hairline and down along the temples and the side of the face. The shield is of a flexible material allowing the bending and forming along the contour of the face while being rigid enough to retain its shape and form a shield spaced from the patient's face.

BRIEF DESCRIPTION OF THE DRAWINGS

Other advantages of the invention will become apparent to those skilled in the art from the following detailed description of the invention in conjunction with the accompanying drawings in which.

DETAILED DESCRIPTION OF THE INVENTION

The present invention is directed to a transparent, light weight, flexible protective shield to be worn over the face of a patient after surgery. More particularly the shield is designed to provide a water proof seal across the forehead and along the sides of the face of the patient adjacent the hairline to enable the patient to shower and wash their hair without the risk of the bandages or splints getting wet. The novel face shield according to the invention is constructed in such a manner to be inexpensive and convenient to use and remove without the problem of ear pieces or ties obstructing the shampooing procedure.

Figure 1:
FIG. 1 is a perspective view of the face shield during use as seen from the left side of a patient.
Figure 2:
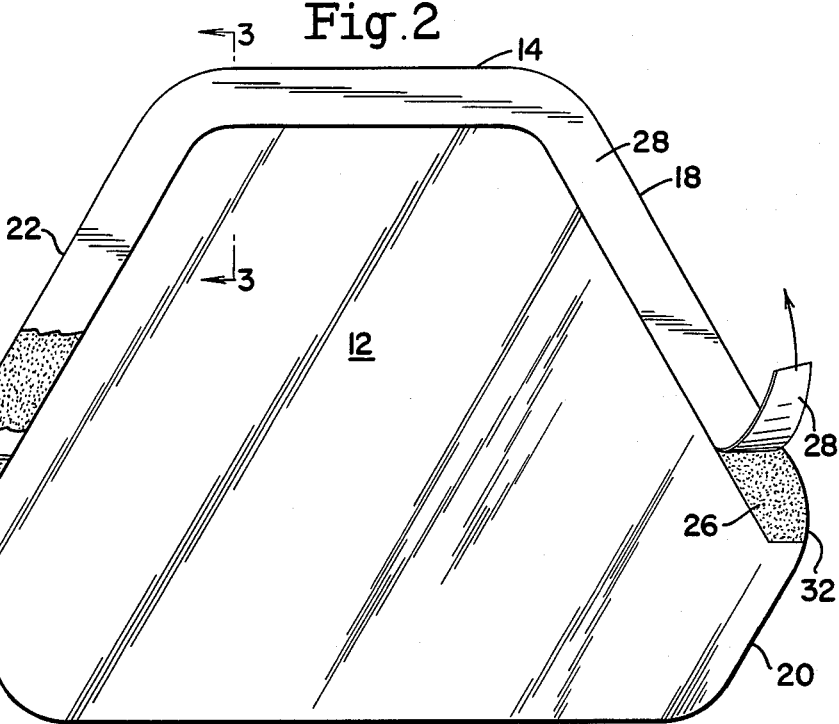
FIG. 2 is a front perspective view of a face shield constructed in accordance with the preferred embodiment of the invention.
Figure 3:
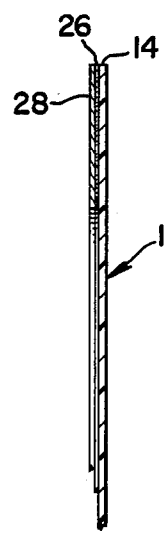
FIG. 3 is a cross sectional view of the novel face shield as seen along line 3—3 of FIG. 2.
Figure 4:
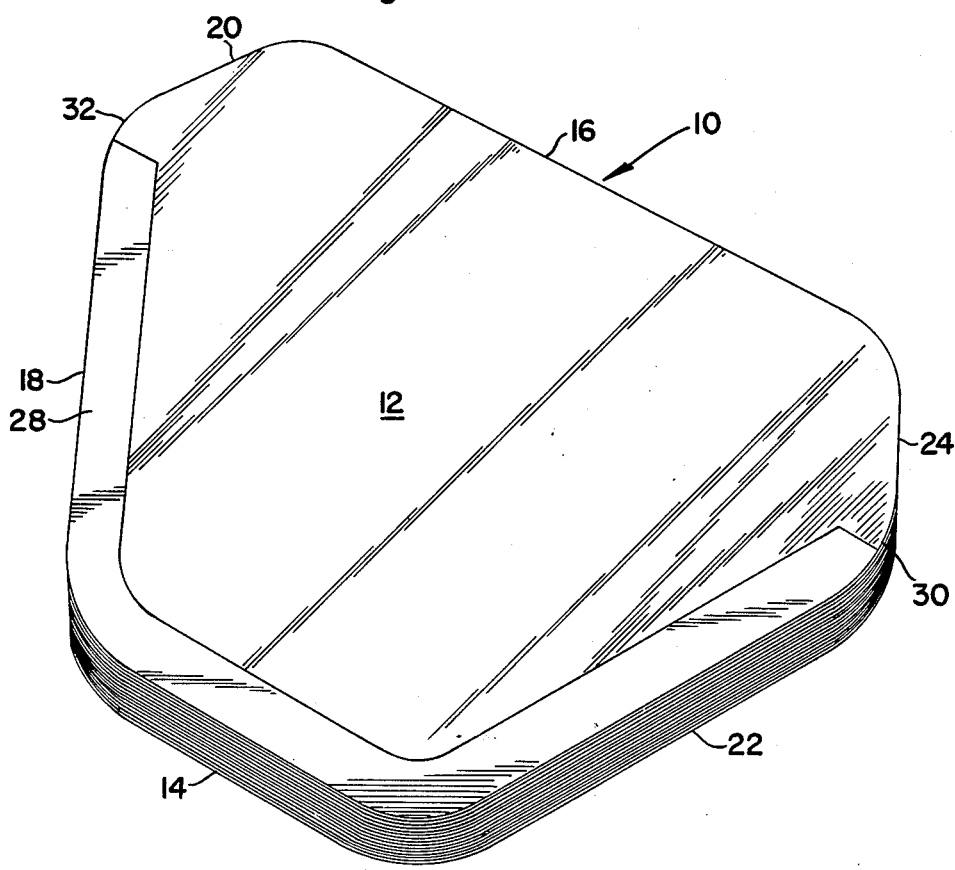
FIG. 4 is a view of a nest of protective face shields wherein each shield protects the adhesive sealing means of the adjacent shield.

Referring to FIG. 1 the face shield is shown comprising a body 10 of a sheet of transparent flexible plastic material in a shape adapted to fit conveniently and comfortably around the contour of a patient's face. The face shield as seen in FIG. 2 is in the flat relaxed configuration. In the preferred form of the invention the face shield 10 is formed from flat sheet material which is cut into the desired shape and size using conventional dies and cutting techniques. Alternatively the face shield can be preformed having a slight convex shape to the shield to maintain the shield in a spaced relation from the face of the user as discussed hereafter in greater detail.

As can be seen in FIG. 2 the face shield according to the preferred embodiment of the invention includes a viewing portion 12 with an essentially hexagonal shape. The face shield 10 has a horizontal upper edge 14 and a parallel bottom edge 16. The hexagonal shape of the face shield 10 forms opposite sides comprising an upper right side edge 18, a lower right side edge 20, an upper left side edge 22 and a lower left side edge 24.

In the preferred form of the invention the face shield is formed of a light weight clear flexible sheet material which can be easily cut and formed. It is desirable that in addition to being flexible the sheet material should be sufficiently rigid to be self supporting such that when conformed to the contour of the face the shield will taken on a cylindrical shape without collapsing as best shown in FIG. 1. It has been found that the shield can be formed from any clear flexible sheet material ranging in thickness between 0.003 and 0.1 of an inch.

Although any clear flexible sheet material can be used the preferred materials include the acrylates, styrenes, polyvinylchlorides, polyamides, polyolefins, vinyls, fluorocarbons, polycarbonates and the cellulose acetates. The thickness of the sheet material will depend on the particular material used to ensure sufficient flexibility without sacrificing the need of the material to be self supporting. The material selected is generally inexpensive such that the shield can be manufactured at a low cost and be disposed of after each use. In the preferred embodiment the body is formed from polycarbonates, acetates and vinyls with a thickness of 0.010 or 0.020 inch.

Referring back to FIG. 2 the face shield 10 is provided with an adhesive strip 26 adjacent the upper edges. In the preferred form the adhesive strip extends adjacent the upper edge 14 and continues downwardly along the upper right edge 18 and the upper left edge 22 to the apex 30 and 32 of the upper and lower sides 22, 24 and 18, 20 respectively. Depending on the intended use and the final desired shape when applied to the face the actual areas provided with adhesive may be varied.

The adhesive used may be any waterproof or water resistant adhesive commonly available such as the silicone resins. The preferred form of the invention employs a pressure sensitive adhesive is provided with a means to protect the adhesive such as a peelable protective release strip 28 which can be readily removed to expose the adhesive as demonstrated in FIG. 2. By employing the use of a peelable release strip it is possible to expose the adhesives only in those areas which are desired to leave the undesired adhesive areas covered. In this respect the pealable release strip can be serrated at particular places to permit the strip to be easily cut or torn in order to leave a desired portion of the strip covering selected areas of the adhesive layer. Alternatively, the adhesive may be rupturable microcapsules or a double faced adhesive tape which can be applied to selective areas as desired.

A further embodiment employs a pressure sensitive adhesive strip without a removable protective release strip. In this embodiment a plurality of the face shields constructed according to the invention can be packaged in a stacked or nested relationship such that the shields are adhered to one another in an array thereby protecting the adhesive strip on each face shield. When a shield is needed the user simply peels off a single shield from the stack thereby exposing the adhesive strip and applies the protective shield to the face as described hereafter in greater detail. In this manner the remaining stack of face shields are kept intact and clean.

Referring to FIG. 1 the face shield according to the invention is shown in use as applied to the patient. To use the face shield the peel strip 28 is removed to expose the adhesive 26. The upper edge 14 of the shield is adhered to the forehead of the patient adjacent the hairline. The upper right and left edges 18 and 22 respectively are then secured to the sides of the face in a continuous fashion down the side of the face to the jaw. The continuous adhesive strip 26 and the flexibility of the face shield 10 permit a continuous waterproof seal thereby forming an effective shield to maintain the bandages and splints in a dry condition.

As can be seen in FIG. 1 the flexibility of the viewing portion 12 of the face shield produces a tent-like structure leading away from the forehead downwardly over the nose and extending beyond the chin of the patient. In the preferred form the face shield 10 is of sufficient dimensions to permit the shield to be slightly spaced from the face to avoid interference and discomfort with the bandages and splints. Similarly the face shield can be preformed to have a slightly convex shape to maintain a space between the shield and the bandages.

The face shield constructed according to the invention is simple and inexpensive to manufacture and can be produced at a cost whereby the face shield can be disposed of after use. By producing a face shield of a disposable material a sterile condition can be ensured to prevent and reduce the risk of infection to the patient.

The novel face shield is easy to apply and to remove and enables the patient to conveniently shower and shampoo regularly without having to remove or replace the bandages and without the risk of infection or irritation to the sensitive areas after surgery due to the water or soap inadvertently contacting the facial areas.

As shown in FIG. 1 the face shield when constructed and applied according to the present invention enables the patient to move their head freely in the shower without risk of exposing the facial areas. The size of the shield in the preferred form is sufficient to extend from the forehead downward past the chin. The shield may be manufactured in a variety of sizes depending on the size of the patient and the areas intended to be protected.

In an alternative embodiment the face shield may be coated with an anti-fogging composition to prevent or reduce the shield from fogging while being worn. In addition, the shield can be coated with a thin layer of a bacteriocide such as hexachlorophene, and tetramethylthiaramidisulfide to maintain a sterile environment. A deodorant or fragrance can similarly be applied to the mask if desired.

The face shield of the invention is relatively light weight and can be packaged in any desired configuration due to the flexibility of the material. The preferred form of packaging is however in the flat configuration such that the shields can be stacked in a compact and efficient manner.

A further alternative embodiment utilizes an additional sealing element such as a foam rubber gasket adajacent the adhesive strip to ensure a water tight seal around the face shield. Additionally, the face shield may include a flexible and deformable gasket-like element along the upper and side edges to which the adhesive layer may or may not be applied. In the embodiment of the invention including the adhesive the gasket-like material is adhered to the forehead and sides of the face of the patient in a similar manner discussed above. When the gasket-like material does not include an adhesive a suitable tie or elastomeric band can be used to hold the shield in place.

The face shield may be further constructed without any adhesive having been applied. In this embodiment the face shield can be secured to the patient by using standard waterproof surgical adhesive tape applied around the edge of the shield to form a water tight seal at the time the shield is applied to the patient.

Although the preferred embodiment of the invention envisions using the face shield during showering, shampooing and haircuts the shield can be worn in any environment where the incisions may be subjected to a risk of infection due to air born bacteria. The novel face shield can further be used by beauticians during various hair treatments such as drying or waving to prevent these harmful chemicals from getting into the eyes and face of a customer patient that has had facial surgery.

The foregoing detailed description of the invention is provided primarily for purposes of illustrating the preferred embodiment of the invention. It will be recognized by those skilled in the art that the preferred embodiment is not intended to be limited to the particular structures and method of operation as they may be readily modified. It will be further readily apparent to those skilled in the art that numerous other modifications not mentioned herein can still be made without departing from the spirit and scope of the invention as claimed in the following claims.

What is claimed is:

1. A protective face shield for a wearer comprising:
   (a) a substantially flat transparent, flexible waterproof sheet material of a hexagonal geometric shape having an upper edge, and an upper and a lower side edge on each side, said upper edge and said upper and lower side edges on each side together forming a frustro trapezium shape with the bottom edge extending beyond the chin over the face of said wearer;
   (b) A water resistant adhesive sealing means extending adjacent said upper and upper side edges, said sealing means for forming a continuous water right seal against the perimeter of the face of said wearer to form a tent-like structure of greater rigidity than said flat sheet material when applied to the perimeter of the face of said wearer to trail shower water away from the face; and
   (c) means for protecting said adhesive sealing means prior to applying the face shielded to said perimeter of said face.

2. The protective face shield of claim 1 wherein said sheet material is a vinyl film of about 0.003 to 0.020 of an inch in thickness.

3. The protective face shield of claim 1 wherein said sheet material has a thickness between 0.003 and 0.02 of an inch.

4. The protective face shield of claim 1 wherein said adhesive sealing means is an adhesive disposed directly on the inside upper edge of said sheet material to seal against a forehead of said wearer.

5. The protective face shield of claim 4 wherein said adhesive means is a continuous coating from said upper edge to said upper side edges to seal against opposite sides of the face adjacent to the hairline of said wearer.

6. The protective face shield of claim 1 wherein said sheet material when attached to said wearer extends downwardly from the forehead of said wearer and is spaced from the face of said wearer and extends at least to the chin of said wearer.

7. The protective face shield of claim 1 wherein said adhesive coating means is a pressure sensitive adhesive strip.

8. The protective face shield of claim 1 wherein said means for protecting said adhesive sealing means is a peelable release strip.

9. A nest comprising several nestable protective face shields for a wearer wherein each protective face shield comprises:
(a) a substantially flat transparent flexible waterproof sheet material of a hexagonal geometric shape having an upper edge, and an upper and a lower side edge on each side said upper edge and said upper and lower side on each side together forming a frusto-trapezium shape with a bottom edge over the face of said wearer and
(b) a water resistant adhesive sealing means extending adjacent said upper edge and said upper side edges, said sealing means for forming a continuous water tight seal against the perimeter of the face of said wearer to form a tent-like structure of greater rigidity than said flat sheet material when applied to the perimeter of the face of said wearer to trail shower water away from the face, and wherein each protective face shield abuts the adhesive sealing means of the adjacent protective face shield and protects said adhesive sealing means.

10. The protective face shield of claim 1 wherein said sheet material is preformed having a slight convex shape.

11. The protective face shield of claim 1 wherein said sheet material is flat.

12. The nest of nestable protective face shields of claim 9 wherein for each the individual face shield in the nest said upper edge of said flexible body is adapted to be attached to the forehead adjacent a hairline and said first and second side edges of said body edge are attached to the sides of the face of said wearer by said adhesive means and said lower edge of space from the chin of said wearer.

13. The nest of nestable protective face shields of claim 9 wherein for each of the individual face shields in the nest said adhesive means comprises a continuous strip of adhesive coating on said body adjacent to said upper and first and second side edges.

14. The nest of nestable protective face shields of claim 9 wherein for each individual face shield in the nest said sheet material is preformed having a slight convex configuration.

15. The nest of nestable protective face shields of claim 9 wherein for each of the individual face shields in the nest said body has an essentially hexagonal configuration.

16. A waterproof protective post operative face shield comprising;
(a) a transparent substantially flat planar thin film deformable and flexible body having an essentially hexagonal shape defining an upper edge, right and left upper edges, right and left lower edges and a bottom edge;
(b) waterproof adhesive sealing means adjacent said upper edge and said right and left upper edges, said adhesive means being adapted for conforming and attaching said body to the forehead and sides of the face of a user thereby forming a waterproof protective face shield to form a tent-like structure of a greater rigidity than when said thin film is in said substantially flat configuration to trail shower water away from the face of said user; and
(c) protecting means for protecting said adhesive sealing means prior to applying said protective face shield to said user said protecting means comprising a peelable protective release strip.

17. The waterproof protective post operative face shield of claim 16 wherein said thin film deformable and flexible body is composed of a polyvinylchloride film.

* * * * *